United States Patent
Borody (10) Patent No.: US 7,624,736 B2
(45) Date of Patent: Dec. 1, 2009

(54) ORAL OXYGENATING APPLIANCE

(76) Inventor: Thomas J. Borody, Level 1, 144 Great North Road, Five Dock, New South Wales 2046 (AU)

(*) Notice: Subject to any disclaimer, the term of this patent is extended or adjusted under 35 U.S.C. 154(b) by 244 days.

(21) Appl. No.: 10/568,258

(22) PCT Filed: Aug. 9, 2004

(86) PCT No.: PCT/AU2004/001060
§ 371 (c)(1), (2), (4) Date: Jun. 30, 2006

(87) PCT Pub. No.: WO2005/016142
PCT Pub. Date: Feb. 24, 2005

(65) Prior Publication Data
US 2006/0278238 A1    Dec. 14, 2006

(30) Foreign Application Priority Data
Aug. 13, 2003   (AU) ............................. 2003904278

(51) Int. Cl.
*A61F 5/56*   (2006.01)
*A62B 9/06*   (2006.01)
*A61M 15/08*  (2006.01)
*F24J 3/00*   (2006.01)
*A61M 16/00*  (2006.01)

(52) U.S. Cl. ............. 128/848; 128/207.17; 128/207.18; 128/204.17; 128/204.18; 128/200.26

(58) Field of Classification Search ............ 128/207.14, 128/200.26, 848, 201.23, 202.27, 204.12, 128/204.18, 859, 207.29, 207.17, 207.18, 128/206.11, 204.23, 204.22, DIG. 26, 860, 128/861, 862, 203.22, 203.12; 600/431
See application file for complete search history.

(56) References Cited

U.S. PATENT DOCUMENTS 3,802,431 A * 4/1974 Farr ....................... 128/207.18

(Continued)

FOREIGN PATENT DOCUMENTS

WO     WO01/95971     12/2001

(Continued)

*Primary Examiner*—Patricia M Bianco
*Assistant Examiner*—Ophelia Hawthorne
(74) *Attorney, Agent, or Firm*—Ballard Spahr LLP (57) ABSTRACT

An endoscopic mouthguard comprising a bite block comprising a generally annular body adapted to be inserted into the mouth of a patient so as to maintain the upper and lower teeth of the patient in a spaced apart relationship and define an endoscopic passage for introduction of an endoscope into the oral cavity of the patient. The bite block includes a gas delivery passage for delivery of a gas to the oral cavity of the patient, and a gas distribution manifold detachably engaged with the bite block. The gas distribution manifold comprises at least one inlet port for receiving gas from a gas supply, at least one nasal outlet port in fluid communication with the inlet port and adapted so as to direct gas to or toward the nasal passages of the patient; and an oral outlet port in fluid communication with the inlet port. The oral inlet port is configured such that when the gas distribution manifold is engaged with the bite block it is in fluid communication with the gas delivery passage, and when the gas distribution manifold is disengaged from the bite block and the bite block is removed from the mouth of the patient, the oral outlet port is adapted to direct gas over or toward the mouth of the patient.

25 Claims, 4 Drawing Sheets

U.S. PATENT DOCUMENTS

| | | | |
|---|---|---|---|
| 4,640,273 A | 2/1987 | Greene et al. | 138/136 |
| 5,174,284 A | 12/1992 | Jackson | 128/200.26 |
| 5,273,032 A | 12/1993 | Borody | 128/207.14 |
| 5,413,095 A | 5/1995 | Weaver | 128/200.26 |
| 5,431,158 A | 7/1995 | Tirotta | 128/206.21 |
| 5,513,634 A * | 5/1996 | Jackson | 128/207.18 |
| 5,575,282 A | 11/1996 | Knoch et al. | 128/204.18 |
| 5,752,510 A | 5/1998 | Goldstein | 128/207.18 |
| 6,679,257 B1 | 1/2004 | Robertson et al. | 128/204.18 |
| 2003/0188750 A1 | 10/2003 | Christopher | 128/207.14 |
| 2004/0129273 A1* | 7/2004 | Hickle | 128/207.14 |
| 2005/0165304 A1* | 7/2005 | Albertelli | 600/431 |

FOREIGN PATENT DOCUMENTS

WO    WO2004/030723    4/2004

* cited by examiner

ORAL OXYGENATING APPLIANCE

CROSS REFERENCE TO RELATED APPLICATIONS

The present application claims priority to Australia Patent Application No. 2003904278, filed Aug. 13, 2003, which application is incorporated herein fully by this reference.

FIELD OF THE INVENTION

The present invention relates to the field of endoscopic mouthguards for maintaining the teeth of a patient in a spaced apart relationship during endoscopic and like procedures to allow the introduction of a medical device into the oral cavity of a patient. More particularly, the present invention relates to an endoscopic mouthguard for allowing the introduction of a medical device into the oral cavity of a patient whilst delivering a gas to the patient.

BACKGROUND OF THE INVENTION

During investigative and surgical procedures, in particular endoscopic procedures, a bite block is typically inserted within the patient's mouth so as to maintain the teeth in a spaced apart relationship so as to allow the introduction of a medical device within the oral cavity of the patient. The bite block prevents the patient from biting upon the medical instrument thus protecting the instrument and preventing the patient's teeth being damaged by the instrument. U.S. Pat. No. 4,604,2783 (Green et al.) discloses a device having an annular body which is sufficiently rigid to resist compression and is provided with a relatively soft outer layer to cushion the patient's bite. Bite blocks such as those disclosed by Green et al. are typically annular or tubular in shape and are used to maintain the upper and lower teeth of a patient in a spaced apart relationship by contacting predominantly the incisor teeth of the patient.

Although such bite blocks protect the patient and medical device, patients undergoing endoscopic procedures whilst under sedation are often observed to undergo hypoxia, that is, the fall of oxygen saturation in the blood below acceptable levels. The degree of hypoxia may be minor which is considered tolerable in younger patients. However, the effects of hypoxia can be more serious and, particular with elderly patients and patients with respiratory and/or cardiovascular disorders, can be dangerous or injurious to health. In such patients, the degree of hypoxia induced by sedation and the obstruction to the airways caused by a bite block and endoscopic instruments, has been known to precipitate cardiac or respiratory arrest. Furthermore, patients suffering from the effects of hypoxia have been observed to recover more slowly from sedation and/or anesthesia and may as a result suffer post-operative complications requiring additional care.

U.S. Pat. No. 5,273,032 (Borody), an earlier patent to the present inventor, describes a bite block which includes integral passages directed at a patient's nostrils from below and internally into the patient's oral cavity when in use. The device includes an inlet for the introduction of oxygen into the integral passages so as to allow continuous insufflation of oxygen during use so as to maintain patient vascular oxygenation.

Another device for oxygenating the oral cavity of a patient is described in U.S. Pat. No. 5,413,095 (Weaver) whereby oxygenation to the patient is achieved by a bite block having two parallel channels formed in the bite block and exiting into the mouth of the patient, the channels being formed to receive a pair of nasal cannulae which extend from a common oxygen supply or a single adapter extending from an oxygen supply tube, so that all oxygen is supplied directly and exclusively to the mouth of the patient.

A further device is described in U.S. Pat. No. 5,513,634 (Jackson), whereby a standard bite block is described to which a manifold having flexible oxygenating nasal prongs is attached, the nasal prongs extending upwards from the manifold into the patient's nostrils to supply supplementary oxygen rich gas to the patient which is separate from the air breathed through the patient's mouth. Nasal prongs of this type have however been found to cause the patient discomfort.

Other disadvantages and shortcomings of prior art tubular bite blocks include concentrated loading to the incisor teeth which may cause damage to the teeth due to increased stresses both during endoscopy and during removal of the bite block. Also, devices which deliver oxygen only to the nasal passages of a patient can cause patients to develop nose bleeds due to dryness caused to the nasal canal. Furthermore, a significant portion of patients do not breathe nasally during or after endoscopic procedures for a variety of physical or physiological reasons and as such, can be deprived of oxygen.

A further and recurrent problem with bite blocks of the prior art is the rather small oral opening provided through the bite block which does not allow the introduction of a large dilator such as a Fr 60, which has a diameter of 20 mm. During a dilation procedure in which a large dilator is to be used, the bite block must first be removed from the patient and an alternate obturator, such as a large syringe, must be inserted prior to the dilation procedure taking place.

Any discussion of documents, publications, acts, devices, substances, articles, materials or the like which is included in the present specification has been done so for the sole purpose so as to provide a contextual basis for the present invention. Any such discussions are not to be understood as admission of subject matter which forms the prior art base portion, or any part of the common general knowledge of the relevant technical field in relation to the technical field of the present invention to which it extended at the priority date or dates of the present invention.

SUMMARY OF THE INVENTION

A first aspect of the present invention provides an endoscopic mouthguard comprising:

a bite block comprising a generally annular body adapted to be inserted into the mouth of a patient so as to maintain the upper and lower teeth of the patient in a spaced apart relationship and define an endoscopic passage for introduction of an endoscope into the oral cavity of the patient, the bite block including a gas delivery passage for delivery of a gas to the oral cavity of the patient; and a gas distribution manifold detachably engaged with said bite block, the gas distribution manifold comprising:

at least one inlet port for receiving gas from a gas supply;

at least one nasal outlet port in fluid communication with the inlet port and adapted so as to direct gas to or toward the nasal passages of the patient; and an oral outlet port in fluid communication with the inlet port and configured such that when the gas distribution manifold is engaged with the bite block the oral outlet port is in fluid communication with the gas delivery passage, and when the gas distribution manifold is disengaged from the bite block and the bite block is removed from the mouth of the patient the oral outlet port is adapted to direct gas over or toward the mouth of the patient.

The at least one nasal port may comprise a pair of apertures arranged such that gas flowing from said apertures is directed toward the patient's nostrils from a position below the nose of the patient. Alternatively, the gas distribution manifold may include a pair of tubular portions each adapted to extend at least partly into each nostril of the patient and defining two nasal outlet ports.

The at least one nasal port may comprise a single elongate aperture, the single elongate aperture extending laterally to the patient in use such that gas is delivered to both nostrils of the patient.

The oral outlet port may comprise a generally elongate aperture extending laterally relative to the patient in use.

The gas distribution manifold may be detachably engaged with the bite block by at least one frangible portion extending between the bite block and the gas distribution manifold.

Alternatively, the bite block and the gas distribution manifold each further include respective cooperating engagement means configured such that the gas distribution manifold is detachably and attachably engageable with the bite block. Preferably the respective cooperating engagement means comprise compliant interlocking formations integrally formed with the gas distribution manifold and the bite block.

The gas delivery passage may comprise a first portion which is integrally formed with the annular body and defines a gas flow passage between the oral cavity and a front region of the annular body, and a second portion which provides a connection between the oral outlet port and the first portion, said second portion having a distal end adapted to engage with the oral outlet port to provide gas communication between the oral outlet port and the gas delivery passage. The gas delivery passage is preferably of slot shape in cross-section with the longitudinal axis of the slot shape extending transverse to the axis of the annular body.

The gas delivery passage may be integrally formed with the annular body and arranged such that when in use, the gas delivery passage is positioned superiorly to the endoscopic passage. Preferably the gas delivery passage terminates in a rearward facing opening which is arranged so as to deliver gas toward the rear of the oral cavity.

The gas distribution manifold may include a tubular connector extending from the inlet port, said connector having a distal end engageable with a gas supply conduit.

The endoscopic mouthguard may further include at least one obturator engagement formation integrally formed with the bite block, wherein the at least one obturator engagement formation provides an attachment point for an obturator member, the obturator member adapted to be used for depressing a patient's tongue to thereby provide improved access to the pharynx of the patient.

Preferably the endoscopic passage has a diameter of at least 20 mm so as to allow the passage of a 60Fr dilator therethrough.

An outer surface of the annular body may include a contact portion adapted to be engaged by the teeth of the patient when the annular body is operatively positioned within the mouth of the patient. A cushioning member may be affixed to the contact portion so as to distribute the load imparted to the bite block by the patient's teeth. The bite block may include an outer peripheral flange adapted to overlie the lips of the patient. The bite block and the gas distribution manifold may be formed from a resilient polymeric material. The gas distribution manifold may further include an attachment means for securing the gas distribution manifold to the patient.

A second aspect of the present invention provides a gas distribution manifold for providing a gas to a patient, the gas distribution manifold comprising:

at least one inlet port for receiving a gas from a gas supply;

at least one nasal outlet port in fluid communication with the inlet port and adapted to direct gas to the nasal passages of the patient; and an oral outlet port in fluid communication with the inlet port and adapted to direct gas over or toward the mouth of the patient.

Preferably the gas distribution manifold is detachably engageable with an oxygenating bite block having a gas delivery passage, such that when attached to the bite block, the oral outlet port is in fluid communication with the gas delivery passage so as to deliver gas to the oral cavity of the patient.

A third aspect of the present invention provides a method of delivering a gas to the nasal passages and the mouth of a patient, wherein the gas is delivered to the nasal passages from below the nose and over or toward the mouth from above the mouth of the patient from a gas distribution manifold;

wherein the gas distribution manifold comprises:

at least one inlet port for receiving gas from a gas supply;

at least one nasal outlet port in fluid communication with the inlet port and adapted to direct gas to or toward the nasal passages of the patient; and an oral outlet port in fluid communication with the inlet port and configured to direct gas over or toward the mouth of the patient.

Preferably the gas is delivered to the patient during recovery from anesthesia, and more preferably the gas is an oxygen rich gas.

Throughout the specification the term "comprise" and variations on this term including "comprising" and "comprises" are to be understood to imply the inclusion of a feature, integer, step or element, and not exclude other features, integers, steps or elements.

These and other advantages of the present invention will become apparent reading the following description.

BRIEF DESCRIPTION OF THE DRAWINGS

The invention now will be described, by way of example only, and with reference to the accompanying drawings in which.

DETAILED DESCRIPTION OF THE DRAWINGS

The following description refers to preferred embodiments of the endoscopic mouthguard of the present invention. To facilitate an understanding of the invention, reference is made in the description to the accompanying drawings whereby the mouthguard is illustrated in preferred embodiments. Similar components between the drawings are identified by the same reference numerals.

Figure 1A:
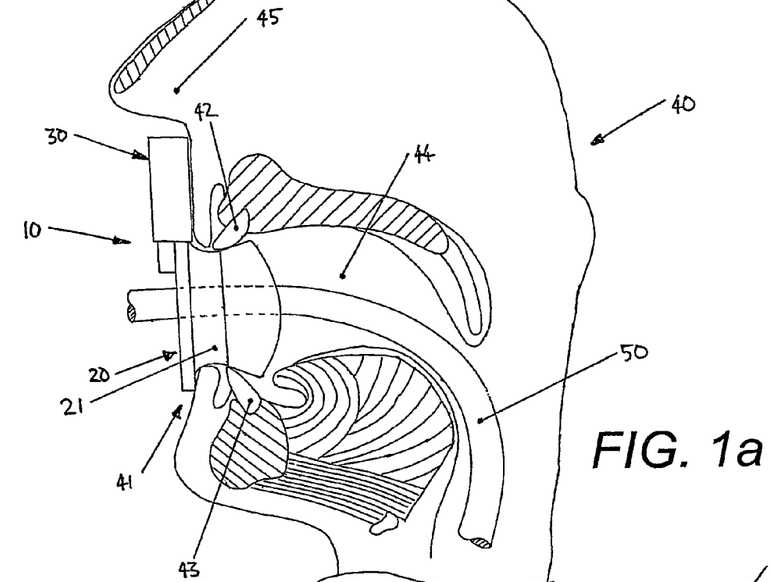
FIG. 1a shows a schematic view of an endoscopic mouthguard according to the invention in situ through the sagittal plane of a patient.
Figure 1B:
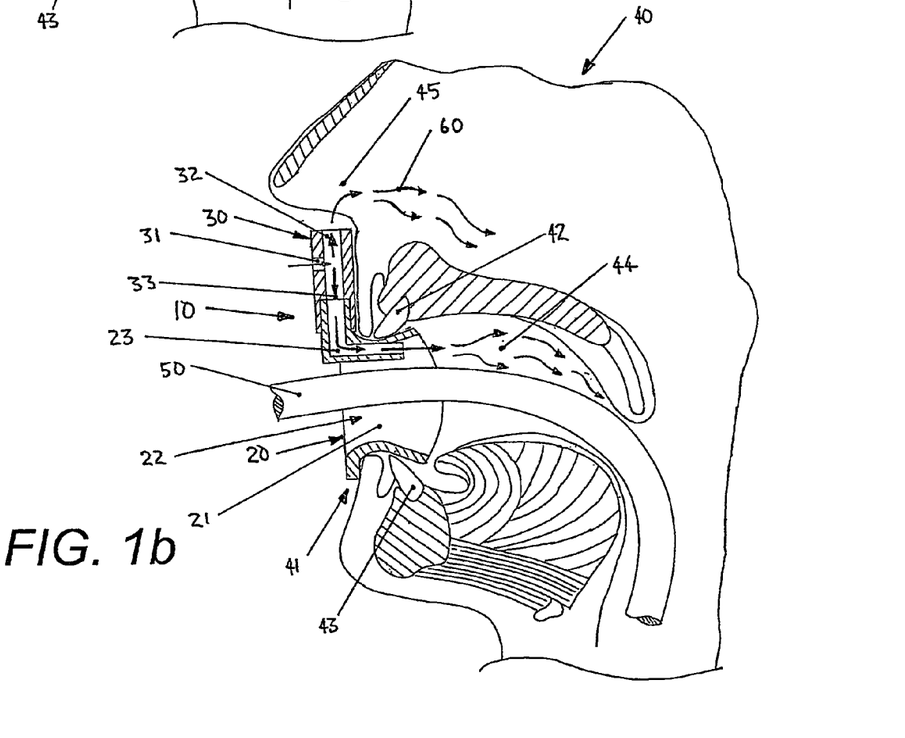
FIG. 1b shows a sectional view of the endoscopic mouthguard shown in FIG. 1a in situ through the sagittal plane of the patient.

Referring to the drawings, FIGS. 1a and 1b depict a schematic sagittal view of the manner in which certain features of one aspect of the present invention are arranged in relation to one another. An endoscopic mouth guard 10 is shown comprising a bite block 20 and a gas distribution manifold 30 detachably engaged with the bite block 20. The bite block 20 comprises a generally annular body 21 and is adapted to be inserted into the mouth 41 of a patient 40 so as to maintain the upper teeth 42 and the lower teeth 43 of the patient 40 in a spaced apart relationship so as to define an endoscopic passage 22 for the introduction of an endoscopic device 50 into the oral cavity 44 of the patient 40. The bite block 20 further comprises a gas delivery passage 23 for delivery of a gas denoted by arrows 60 to the oral cavity 44 of the patient 40.

The endoscopic mouthguard 10 further comprises a gas distribution manifold 30 which is detachably engaged with the bite block 20. The gas distribution manifold 30 comprises an inlet port 31 for receiving gas 60 from a gas supply and at least one nasal outlet port 32 in fluid communication with the inlet port 31 and adapted to direct gas 60 to or toward the nasal passages 45 of the patient 40 from below the patient's nose.

The gas distribution manifold 30 further comprises an oral outlet port 33 in fluid communication with the inlet port 31 and configured such that when the gas distribution manifold 30 is engaged with the bite block 20 as illustrated, the oral outlet port 33 is in fluid communication with the gas delivery passage 23 such that gas is directed into the oral cavity 44 of the patient.

Figure 2A:
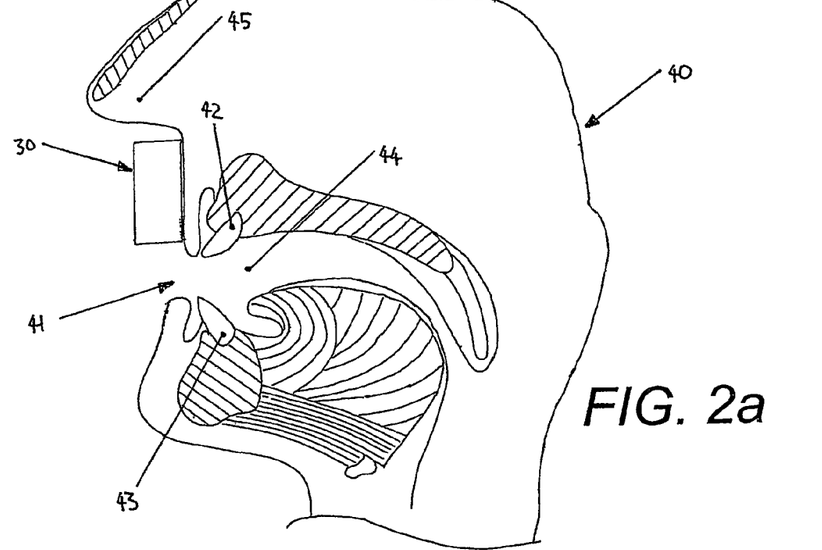
FIG. 2a shows a schematic view of a gas distribution manifold according to the present invention in situ through the sagittal plane of a patient.
Figure 2B:
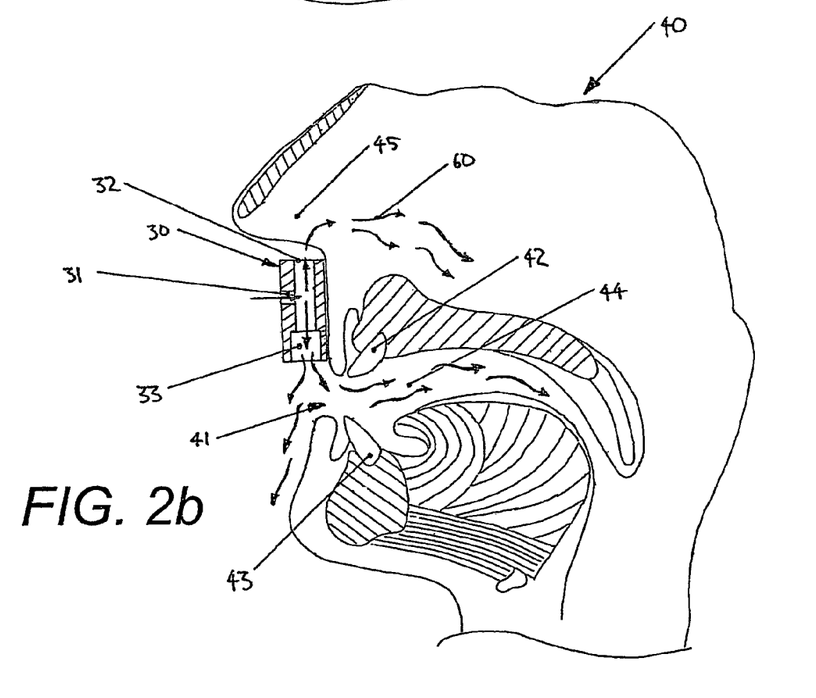
FIG. 2b shows a sectional view of the gas distribution manifold shown in FIG. 2a in situ through the sagittal plane of the patient.

Referring to FIGS. 2a and 2b, when the gas distribution manifold 30 is disengaged from the bite block 20 of FIGS. 1a and 1b, the bite block is removed from the mouth 41 of the patient 40 and the gas distribution manifold 30 is maintained in approximately the same position in relation to the patient as when engaged with the bite block 20. The oral outlet port 33 is adapted such that gas 60 is directed over or toward the mouth 41 of the patient 40, whilst gas 60 is still directed to or towards the nasal passages 45 of the patient 40.

It will be understood that the invention as broadly described with reference to FIGS. 1a, 1b, 2a and 2b is schematic account of the manner in which the present invention functions. Geometric or physical limitations are not implied and should not be inferred by the schematic representative features of the present invention, nor are structural limitations implied or suggested.

Figure 3A:
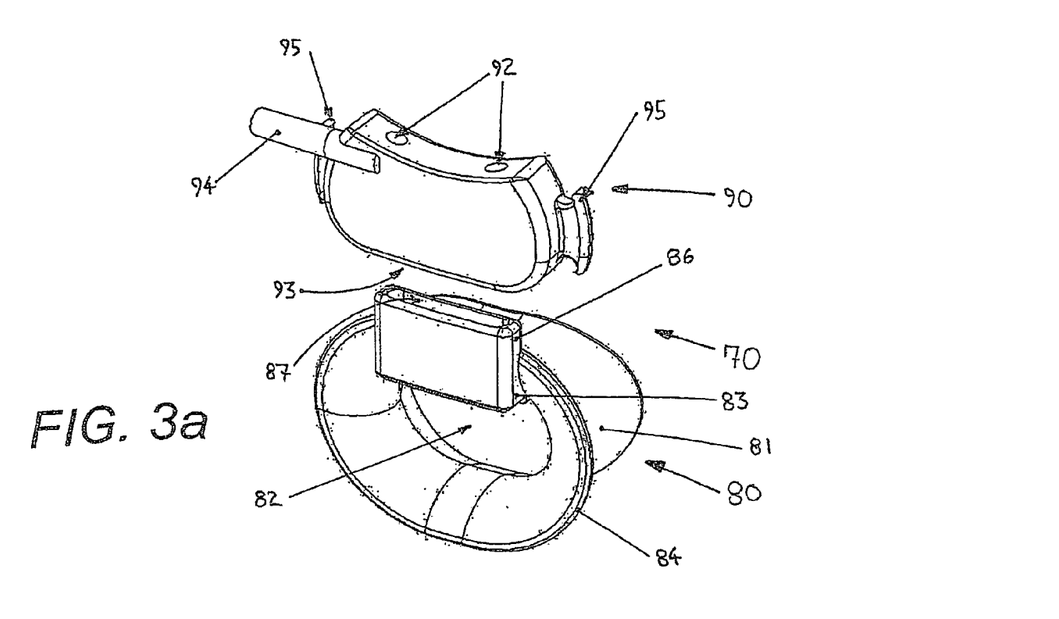
FIG. 3a shows an anterior perspective view of an embodiment of the present invention in an exploded arrangement.
Figure 3B:
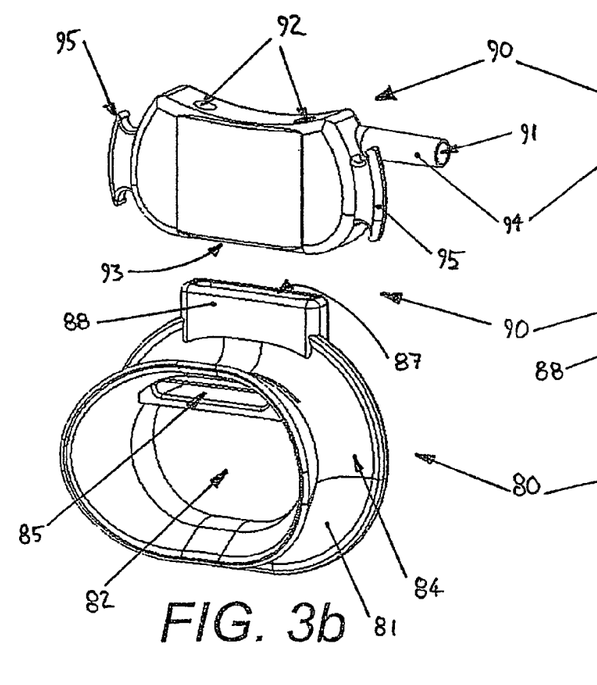
FIG. 3b shows a posterior perspective view of the embodiment of FIG. 3a in an exploded arrangement.
Figure 3C:
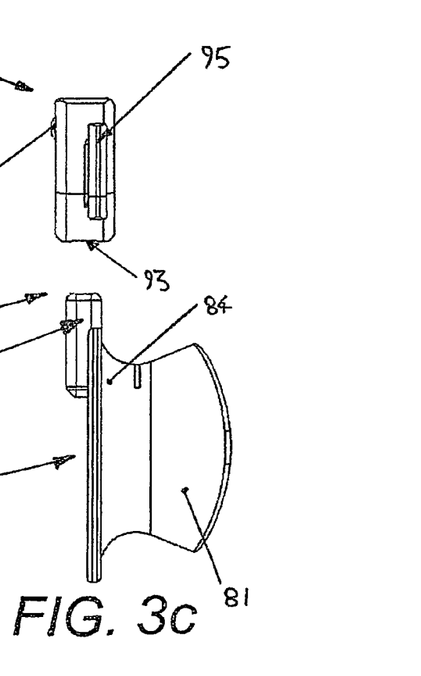
FIG. 3c shows a side view of the embodiment of FIGS. 3a and 3b in an exploded arrangement.

Referring to FIGS. 3a, 3b and 3c, an embodiment of an endoscopic mouthguard 70 according to the present invention is depicted having similar structural and functional features as broadly described with reference to FIGS. 1a, 1b, 2a and 2b. The endoscopic mouthguard 70 comprising an annular bite block 80 and a gas distribution manifold 90 depicted as being disengaged from the bite block 80.

The annular body 81 of the bite block 80 defines an endoscopic passage 82 having a diameter of at least 20 mm so as to allow the introduction of an endoscopic or medical device, for example an 60Fr dilator, to the oral cavity of a patient. Such an endoscopic passage 82 allows the introduction of a variety of medical devices into the oral cavity of a patient and does not restrict the mouthguard 10 to use with small endoscopic devices, but rather a variety of devices used in examination, diagnosis and treatment of a patient.

The bite block 80 includes an outer peripheral flange 84 which is adapted to overlie the lips of the patient when the bite block 80 in use. The outer peripheral flange 84 allows the bite block 80 to be seated appropriately within the patient's mouth and assists in location and removal of the bite block 80.

In this embodiment, the gas delivery passage 83 is integrally formed with the bite block 80 and is of a generally elongate tubular configuration and arranged such that when in use, the gas delivery passage 83 is positioned superiorly to the endoscopic passage 82. The gas delivery passage 83 terminates in a distal opening 85 which is arranged so as to deliver gas toward the rear of the oral cavity of a patient when the bite block 80 is positioned within the mouth of the patient. The bite block 80 includes a tubular portion 86 extending from the bite block 80 towards the gas distribution manifold 90 and in fluid communication with the gas delivery passage 83, the gas delivery passage 83 terminating at a proximal opening 87. In this embodiment, the tubular portion 86 and the proximal opening 87 are generally elongate and extend laterally relative to the patient when in use.

The gas distribution manifold 90 includes a tubular connector 94 extending from the gas distribution manifold 90 defining the inlet port 91 for receiving gas from gas supply. The tubular connector 94 is sized such that it may be received within a gas delivery conduit from the gas supply. The tubular connector 92 may include at least one barb, detent arrangement, or an appropriately textured surface so as to assist in the engage with the gas delivery tube. The gas distribution manifold 90 may include a further inlet port for the introduction and delivery to a patient of a further gas, although only one inlet port is depicted in the embodiment as illustrated.

The gas distribution manifold 90 further includes a pair of nasal outlet ports 92 in the form of a pair of apertures in this embodiment, being in fluid communication with the inlet port 91 and which are arranged so as to direct gas to or toward the nasal passages of the patient from below the patient's nose. The gas distribution manifold may alternatively include a single elongate aperture defining the nasal outlet port and be arranged so as to extend laterally in relation to the patient when in use. Alternatively, the gas distribution manifold 90 may further include a pair of tubular portions extending towards the nose of the patient and defining the nasal outlet ports such that gas is delivered directly into the nasal passages of the patient. Such tubular portions may extend at least partially within the nostrils of the patient and be appropriately rounded so as to minimise patient discomfort. Minor variations on the manner in which the nasal outlet port is formed are understood to fall within the scope of the present invention.

In this embodiment, the oral outlet port 93 is in the form of an elongate aperture and is arranged so as to extend laterally relative to the patient when in use. The oral outlet port 93 is further arranged such that when the gas distribution manifold 90 is disengaged from the bite block 80, the oral outlet port 93 directs gas over or toward the mouth of the patient whilst maintaining gas supply to the nasal passages. It is to be understood that the gas distribution manifold 90, in this embodiment, includes internal passages joining the inlet port 31, the nasal outlet ports 32 and the oral outlet port 33 in fluid communication, and the manner in which the ports are connected and sized is such that appropriate amounts of gas are supplied to the oral and nasal cavities of a patient.

In this embodiment, the gas distribution manifold 90 further includes two attachment means 95 so as to allow the gas distribution manifold 90 to be attached to the patient when in use. The attachment means 95 are in the form of a protrusion engageable with a strap such that the strap extends from one protrusion to the other protrusion and behind the patient's head. Such a strap may be formed from an elastic material or from a strap including an adjustment means. Alternatively, the gas distribution manifold 90 may be secured to the patient by an adhesive means such as an adhesive tape or band. Another manner in which the gas distribution manifold may be secured to the patient is by the gas supply tube engaged with the inlet port. Although the present embodiment depicts only one gas inlet port, in further embodiments there may exist a second gas inlet thus allowing the gas supply tubes to be used to secure the gas distribution manifold to the patient's head.

Figure 4A:
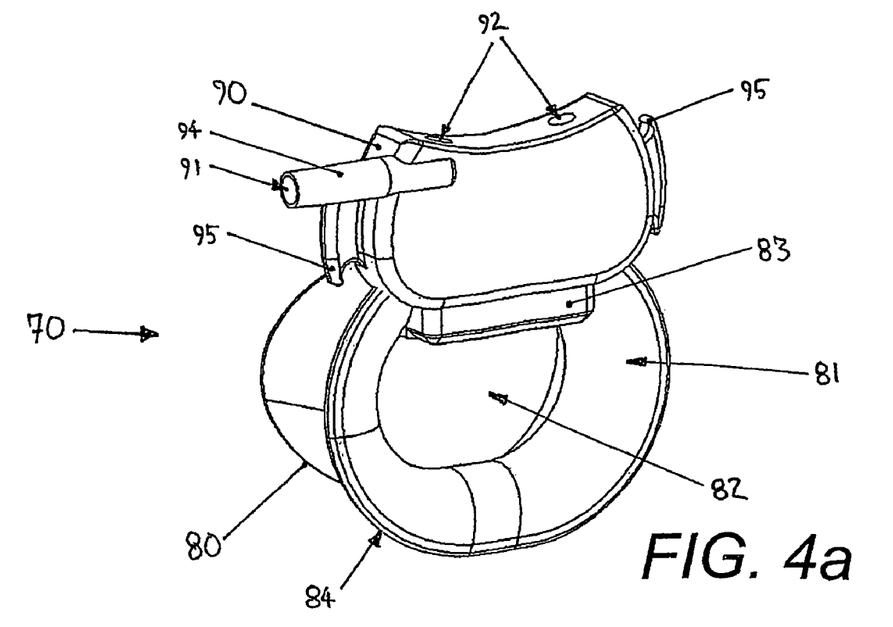
FIG. 4a shows an anterior perspective view of the embodiment of FIGS. 3a, 3b and 3c in an assembled arrangement.
Figure 4B:
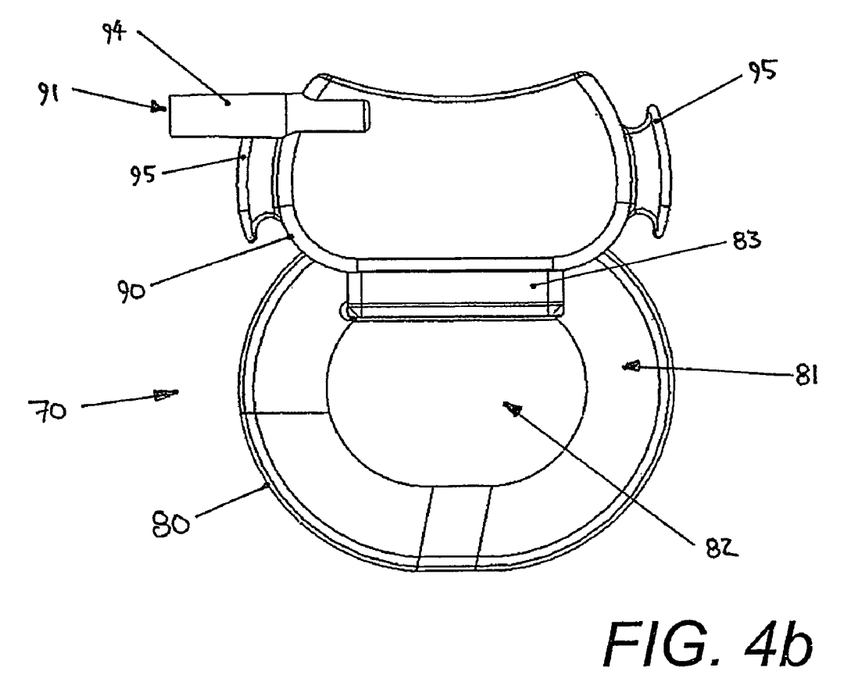
FIG. 4b shows an anterior view of the embodiment of FIGS. 3a, 3b, 3c and 4b in an assembled arrangement.

The oral outlet port 93 of the gas distribution manifold 90 and the tubular portion 86 of the bite block are sized such that the tubular portion 86 is locatable within the oral outlet port 93, as depicted in FIGS. 4a and 4b, whereby the gas distribution manifold 90 and the bite block 80 are depicted in an engaged relationship.

As shown in FIGS. 4a and 4b and as functionally described with reference to FIGS. 1a and 1b, when the gas distribution manifold 90 and bite block 80 are engaged, gas may delivered to the oral cavity and the nasal passages of a patient simultaneously via the gas delivery passage 83 and the nasal outlet ports respectively 92. In this embodiment of the invention, the gas distribution manifold 90 and the bite block 80 are engaged in a sliding or friction grip relationship between the tubular portion 86 and the oral outlet port 93. The sliding relationship is such that the gas distribution manifold 90 and the bite block 80 can be securely engaged in a gas type manner yet easily disengaged when disengagement is required. The gas distribution manifold 90 and the bite block 80 may further include respective cooperating engagement means or formations, and be configured such that the gas distribution manifold 90 is detachably and attachably engageable with the bite block 80. Examples of such engagement means include a elastically deformable protrusion engagable with a complementary non-deformable protrusion in a snap-lock type arrangement formed integrally with the gas distribution manifold 90 and the bite block 80. Alternatively, the gas distribution manifold 90 may be attached to the bite block 80 by one or more frangible portions extending between the gas distribution manifold 90 and the bite block 80 which allow ease of removal of the gas distribution manifold 90 from the bite block 80. An adhesive tape type connection may be used to hold the components together, the tape being removable when disengagement is required.

The gas distribution manifold 90 and bite block 80 in this embodiment are formed from a resilient polymeric material so as to provide patient comfort and minimize risk of damage to a patient's teeth. The annular body 81 of the bite block 80 is arranged so as to provide an engagement with more of the patient's teeth than the patient's incisors so as to distribute the force between a series of teeth and the annular body 81. The annular body 81 is configured so as to be engageable with a cushioning member positionable between the bite block 80 and the patient's teeth, when in use. Such a cushioning member would have suitable mechanical properties so as to deform and distribute the force exerted on the bite block by the teeth so as to reduce the likelihood of damage to the patient's teeth. The cushioning member may be integrally formed with the bite block 80 or engageable with the bite block 80. Alternatively, the cushioning member may be positioned upon the teeth of the patient prior to inserting the bite block 80 within the mouth.

The present invention allows the delivery of a gas to a patient both orally and nasally during endoscopy and similar surgical procedures. Providing a patient with oxygen or an oxygen rich gas via the oral cavity significantly reduces the likelihood of a patient suffering from hypoxia. Furthermore, it is well documented that patients have varying degrees of nasal function during the respiratory process, and that many patients breathe predominantly via the mouth rather than the nose, particularly after a surgical procedure.

The present invention also allows delivery of a gas, preferably an oxygen rich gas, to a patient both orally and nasally whilst the patient is recovering from anesthesia following a surgical procedure. Removal of the bite block 80 from the gas distribution manifold 90 allows the gas to be delivered to the patient's mouth from the oral outlet port 93, whilst still maintaining gas delivery to the patient's nasal passages. The detachability of the bite block 80 from the gas distribution manifold 90 allows the gas distribution manifold 90 to remain attached to the patient and continue to deliver gas to the patient whilst in post-operative/post-investigate recovery from anesthesia. In the case where the bite block 80 and the gas delivery manifold 90 are joined to each other by one of more frangible portions, the bite block 80 and the gas distribution manifold 90 may be separated by flexing the bite block 80 relative to the gas distribution manifold 90 until the frangible portions rupture. Ease of detachability provided by frangible portions or alternatively a clip-lock mechanism or friction grip arrangement allows the bite block to be easily removed and discarded without interrupting gas delivery to the patient for any significant amount of time.

Post-operative oxygenation to a patient can be crucial in the recovery and well-being of a patient. Prior art bite block devices do not typically allow for oxygenation of a patient nasally and orally both during and after a surgical procedure. Previous endoscopic technologies use either non-oxygenating or an oxygenating bite block during endoscopy and when a patient is taken to a recovery room post-operatively, standard nasal prongs are fitted to the patient, and oxygen is delivered nasally by a separate device. However, it is estimated that some 60% or more of patients initially breathe orally during post-endoscopic recovery and as such, oxygen is not effectively delivered to such patients.

It is envisaged that the device according to the present invention will assist in the reduction of hypoxia both during and following endoscopic procedures and the like, and will reduce the incidence of cardiac and respiratory arrest both inter-operatively and post-operatively.

A further advantage provided by the present invention is ease of attachment of an obturator member whilst the bite block remains positioned within the mouth of a patient by the provision of at least one obturator engagement formation integrally formed with the bite block. The obturator engagement formation allows for the engagement of a curved "snap-in" polymeric open-tube obturator through the endoscopic passage. Such an obturator allows the tongue of a patient to be depressed and the oral cavity to be opened so as to permit suction with a suction device, for example a Yanaeur suction device. The "snap-in" obturator may resemble a Guedel airway and may be used to permit mask-assisted ventilation of a patient, in particular during an emergency, without the need to remove the bite block, which is often a difficult task to achieve with sedated patients.

Other advantages of the present invention include reduced incidence of nasal bleeding by the absence of traditional nasal prongs which extend into the nasal passages of the patient, and enhanced and increased protection of a patient's teeth during insertion and removal of the bite block.

It will also be appreciated that the above embodiment of the present invention is merely an example of the invention, and other manners in which to arrange various features so as to allow for gas delivery to a patient in accordance with the present invention are understood to fall within the spirit and scope of the present invention as claimed and described.

It will also be understood that the invention disclosed and defined herein extends to all alternative combinations of two or more of the individual features mentioned or evident from the text or drawings. All of these different combinations constitute various alternative aspects of the invention The foregoing describes an embodiment of the present invention and modifications, obvious to those skilled in the art can be made thereto, without departing from the scope of the present invention.

The invention claimed is:

1. An endoscopic mouthguard comprising:
a bite block comprising a generally annular body adapted to be inserted into the mouth of a patient so as to maintain the upper and lower teeth of the patient in a spaced apart relationship and define an endoscopic passage for introduction of an endoscope into the oral cavity of the patient, the bite block including a gas delivery passage for delivery of a gas to the oral cavity of the patient; and
a gas distribution manifold detachably engaged with said bite block, the gas distribution manifold comprising:
at least one inlet port for receiving gas from a gas supply;
at least one nasal outlet port in fluid communication with the inlet port and adapted so as to direct gas to or toward the nasal passages of the patient; and
an oral outlet port in fluid communication with the inlet port and configured such that when the gas distribution manifold is engaged with the bite block the oral outlet port is in fluid communication with the gas delivery passage,
attachment means for attaching the manifold to the patient so as to hold the manifold in position on the patient when the manifold is disengaged from the bite block;
and when the gas distribution manifold is disengaged from the bite block and the bite block is removed from the mouth of the patient the oral outlet port is adapted to direct gas over or toward the mouth of the patient.

2. An endoscopic mouthguard according to claim 1, wherein the at least one nasal port comprises a pair of apertures arranged such that gas flowing from said apertures is directed toward the patient's nostrils from a position below the nose of the patient.

3. An endoscopic mouthguard according to claim 1, wherein the gas distribution manifold further includes a pair of tubular portions each adapted to extend at least partly into each nostril of the patient and defining two nasal outlet ports.

4. An endoscopic mouthguard according to claim 1, wherein the at least one nasal port comprises a single elongate aperture, the single elongate aperture extending laterally to the patient in use such that gas is delivered to both nostrils of the patient.

5. An endoscopic mouthguard according to claim 1, wherein the oral outlet port is a generally elongate aperture extending laterally relative to the patient in use.

6. An endoscopic mouthguard according to claim 1, wherein the gas distribution manifold is detachably engaged with the bite block by at least one frangible portion extending between the bite block and the gas distribution manifold.

7. An endoscopic mouthguard according to claim 1, wherein the bite block and the gas distribution manifold each further include respective cooperating engagement means configured such that the gas distribution manifold is detachably and attachably engageable with the bite block.

8. An endoscopic mouthguard according to claim 1, wherein the gas delivery passage comprises a first portion which is integrally formed with the annular body and defines a gas flow passage between the oral cavity and a front region of the annular body, and a second portion which provides a connection between the oral outlet port and the first portion, said second portion having a distal end adapted to engage with the oral outlet port to provide gas communication between the oral outlet port and the gas delivery passage.

9. An endoscopic passage according to claim 1, wherein the gas delivery passage is integrally formed with the annular body and arranged such that when in use, the gas delivery passage is positioned superiorly to the endoscopic passage.

10. An endoscopic mouthguard according to claim 1, wherein the gas delivery passage terminates in a rearward facing opening which is arranged so as to deliver gas toward the rear of the oral cavity.

11. An endoscopic mouthguard according to claim 1, wherein the gas distribution manifold further includes a tubular connector extending from the inlet port, said connector having a distal end engageable with a gas supply conduit.

12. An endoscopic mouthguard according to claim 1 further including at least one obturator engagement formation integrally formed with the bite block, wherein the at least one obturator engagement formation provides an attachment point for an obturator member, the obturator member adapted to be used for depressing a patient's tongue to thereby provide improved access to the pharynx of the patient.

13. An endoscopic mouthguard according to claim 1 wherein the endoscopic passage has a diameter of at least 20 mm so as to allow the passage of a 60Fr dilator therethrough.

14. An endoscopic mouthguard according to claim 1 wherein an outer surface of the annular body includes a contact portion adapted to be engaged by the teeth of the patient when the annular body is operatively positioned within the mouth of the patient.

15. An endoscopic mouthguard according to claim 1 wherein the bite block in includes an outer peripheral flange adapted to overlie the lips of the patient.

16. An endoscopic mouthguard according to claim 1, wherein the bite block and the gas distribution manifold are formed from a resilient polymeric material.

17. An endoscopic mouthguard according to claim 1, wherein the gas distribution manifold further includes an attachment means for securing the gas distribution manifold to the patient.

18. An endoscopic mouthguard according to claim 7, wherein the respective cooperating engagement means comprise compliant interlocking formations integrally formed with the gas distribution manifold and the bite block.

19. An endoscopic mouthguard according to claim 8, wherein the gas delivery passage is of slot shape in cross-section with the longitudinal axis of the slot shape extending transverse to the axis of the annular body.

20. An endoscopic mouthguard according to claim 14, wherein a cushioning member is affixed to the contact portion so as to distribute the load imparted to the bite block by the patient's teeth.

21. A method of delivering gas to a patient during and after an endoscopic procedure using apparatus comprising a gas distribution manifold having a gas inlet port, a nasal gas outlet port, an oral gas outlet port, and attachment means for attaching the manifold to the patient, and a annular bite block detachably connected to the manifold, the method comprising the steps of: attaching the apparatus to the patient using the attachment means with the bite block located in the mouth of the patient; supplying gas to the patient via the gas inlet port, the nasal gas outlet port, and the oral gas outlet port; performing an endoscopic procedure on the patient while continuing to supply gas to the patient.

22. A method of delivering gas to a patient during and after an endoscopic procedure to the mouth of a patient according to claim 21, wherein the gas is delivered to the patient during recovery from anaesthesia.

23. A method of delivering gas to a patient during and after an endoscopic procedure to the mouth of a patient according to claim 21, wherein the gas is an oxygen rich gas.

24. A method of delivering gas to a patient during and after an endoscopic procedure according to claim 21, further comprising the step of: allowing the patient to recover while continuing to supply gas to the patient via the nasal gas outlet and the oral gas outlet port.

25. A gas distribution manifold for providing a gas to a patient, the gas distribution manifold comprising:

at least one inlet port for receiving a gas from a gas supply;

at least one nasal outlet port in fluid communication with the inlet port and adapted to direct gas to the nasal passages of the patient; and an oral outlet port in fluid communication with the inlet port and adapted to direct gas over or toward the mouth of the patient;

attachment means for attaching the manifold to the patient so as to hold the manifold in position on the patient when the manifold is disengaged from the bite block;

said gas distribution manifold being detachably engageable with a bite block having a gas delivery passage for delivery of a gas to the oral cavity of the patient;

wherein the oral outlet port is configured such that when the gas distribution manifold is engaged with the bite block the oral outlet port is in fluid communication with the gas delivery passage if the bite block; and when the gas distribution manifold is disengaged from the bite block and the bite block is removed from the mouth of the patient the oral outlet port is adapted to direct gas over or toward the mouth of the patient.

\* \* \* \* \*